(12) United States Patent
de Ketelaere et al.

(10) Patent No.: US 10,458,888 B2
(45) Date of Patent: Oct. 29, 2019

(54) METHOD AND APPARATUS FOR EXAMINING EGGS

(71) Applicant: Katholieke Universiteit Leuven, Leuven (BE)

(72) Inventors: Bart de Ketelaere, Boechout (BE); Catalin Perianu, Wemmel (BE)

(73) Assignee: Katholieke Universiteit Leuven, Leuven (BE)

( * ) Notice: Subject to any disclaimer, the term of this patent is extended or adjusted under 35 U.S.C. 154(b) by 553 days.

(21) Appl. No.: 14/424,692

(22) PCT Filed: Sep. 4, 2013

(86) PCT No.: PCT/EP2013/068288
§ 371 (c)(1),
(2) Date: Feb. 27, 2015

(87) PCT Pub. No.: WO2014/037402
PCT Pub. Date: Mar. 13, 2014

(65) Prior Publication Data
US 2015/0226654 A1    Aug. 13, 2015

(30) Foreign Application Priority Data

Sep. 4, 2012 (GB) .................................. 1215742.6
Sep. 4, 2012 (GB) .................................. 1215743.4
Sep. 4, 2012 (GB) .................................. 1215747.5

(51) Int. Cl.
*G01N 3/08* (2006.01)
*G01N 33/08* (2006.01)
*G01B 11/16* (2006.01)

(52) U.S. Cl.
CPC .............. *G01N 3/08* (2013.01); *G01B 11/16* (2013.01); *G01N 33/08* (2013.01)

(58) Field of Classification Search
CPC ..................................................... G01N 33/08
See application file for complete search history.

(56) References Cited

U.S. PATENT DOCUMENTS

2013/0283894 A1* 10/2013 De Ketelaere ......... A01K 43/00
73/78

FOREIGN PATENT DOCUMENTS

| CN | 102156169 A | 8/2011 |
|---|---|---|
| EP | 0295755 | 12/1988 |
| JP | 64072030 | 3/1989 |

(Continued)

OTHER PUBLICATIONS

"International Application Serial No. PCT/EP2013/068288, International Search Report dated Dec. 20, 2013", 5 pgs.

(Continued)

*Primary Examiner* — Yu-Hsi D Sun
(74) *Attorney, Agent, or Firm* — Schwegman Lundberg Woessner, P.A.

(57) ABSTRACT

A non-destructive method for determining resistance to cracking of an intact egg, whereby said determining comprises at least one of the following steps a) and b):
a) determining a tensile stress developed in an eggshell of said intact egg, for example a tensile stress at a predetermined load;
b) determining an elasticity of said eggshell;
wherein preferably the results of step a) and/or step b) are used in evaluating said resistance to cracking.

36 Claims, 13 Drawing Sheets

(56) References Cited

FOREIGN PATENT DOCUMENTS

| JP | 0416136 A | 1/1992 | |
|---|---|---|---|
| JP | 07072066 | 3/1995 | |
| JP | 2005127720 A | 5/2005 | |
| NL | 1018940 C1 | 3/2002 | |
| RU | 2395958 C2 | 8/2010 | |
| WO | WO 2012060704 A1 * | 5/2012 | ............. A01K 43/00 |
| WO | WO-2016060704 A1 | 5/2012 | |
| WO | WO-2014037402 A1 | 3/2014 | |

OTHER PUBLICATIONS

Kemps, B, et al., "Development of a methodology for the calculation of Young's modulus of eggshell using vibration measurements", Biosystems Engineering 89 (2), (Oct. 2004), 215-221.

Macleod, Niall, et al., "The mechanics and mechanisms of failure of hens' eggs", International Journal of Fracture 142(1-2), (Nov. 2006), 29-41.

Rehkugler, G.E., "Technique for routine stress analysis of the hen's egg", American Society of Agricultural and Biological Engineers 15 (6), (1972), 1086-1090.

Tung, M. A, et al., "Estimation of Young's modulus and failure stresses in the hen's egg shell", Canadian Agricultural Engineering 11 (1), (May 1969), 3-5.

Voisey, Peter W, et al., "Measurement of eggshell strength*", Journal of Texture Studies 5(2), (Jul. 1974), 135-182.

Voisey, Peter W, et al., "Physical properties of egg shells 4. Stress distribution in the shell", British Poultry Science 8(4), (1967), 263-271.

"Chinese Application Serial No. 201380054322.8, Office Action dated Jan. 4, 2016", w/ English Translation, 29 pgs.

"Russian Application Serial No. 2015106845/15, Search Report dated Aug. 28, 2017", w/ English Translation, (dated Aug. 28, 2017), 11 pgs.

Hunton, Peter, "Understanding the architecture of the egg shell", World's Poultry Science Journal 51.2, (1995), 141-147.

Mertens, Kristof, et al., "Monitoring of egg shell strength and egg shell breakage in different production chains of consumption eggs", Proceedings of the XVII European Symposium on the Quality of Poultry Meat and XI European Symposium on the Quality of Eggs and Egg Products, Golden Tulip Parkhotel Doorwerth, Doorwerth, Netherlands, May 23-26, 2005. (WPSA), (2005).

Tamura, Chiaki, et al., "Measurement of eggshell deformation using a non-destructive pressurizing method", Bulletin of the Takikawa Animal Husbandry Experiment Station vol. 21, w/ English Summary, (Mar. 1984), 15-20.

Voisey, PW, et al., "Physical properties of egg shells", British Poultry Science, vol. 8, No. 4, (Jan. 1, 1967), 263-271.

* cited by examiner

METHOD AND APPARATUS FOR EXAMINING EGGS

PRIORITY APPLICATIONS

This application is a U.S. National Stage Filing under 35 U.S.C. 371 from International Application No. PCT/EP2013/068288, filed on 4 Sep. 2013, and published as WO/2014/037402 on 13 Mar. 2014, which application claims the benefit under 35 U.S.C. 119 to United Kingdom Application No. 1215742.6, filed on 4 Sep. 2012 and to United Kingdom Application No. 1215743.4, filed on 4 Sep. 2012, and to United Kingdom Application No. 1215747.5, filed on 4 Sep. 2012; which applications and publication are incorporated herein by reference in their entirety.

TECHNICAL FIELD

The present invention relates to a method and apparatus for examining eggs. The present invention relates in particular to a method and apparatus for determining shell characteristics of eggs.

TECHNICAL BACKGROUND

Although an egg comes with its particular natural defense system (i.e. the eggshell), bacterial contamination of egg contents can nevertheless occur. Commonly, there are two possible ways by which this may happen: within the oviduct before the shell is formed, or through penetration of damaged and inferior quality shells. Whilst both routes are possible, the latter is the more probable. Supposing that unidentified but contaminated eggs find their way into the market place, this could become health hazard for consumers. Moreover, eggs with damaged shells will not be purchased by consumers and this can lead to considerable economic losses. The image of the egg sector strongly suffers from incidences of this kind and this is why breeding companies are looking for alternative selection focuses such as improved egg quality, of which shell quality is of considerable significance.

Commonly, shell quality is used as a synonym for shell strength and defines the capacity of eggshells to endure externally applied loads without cracking or breaking. Shell strength has only moderate heritability, and causes a problem because deteriorating eggshell quality is predominantly expressed late in the laying period. Commercial breeding companies have incorporated eggshell strength in their selection programs for many years. Selection for shell strength is being practiced by primary poultry breeders, using a variety of destructive and non-destructive methods for determining optimal selection variables. The latter have the advantage that the eggs can still be used after measurement, but in view of the low price per egg and EU food safety regulations, this argument carries less weight than speed and accuracy of measurement, heritability and genetic correlation with shell damage under commercial conditions.

A great deal of effort has gone into the design of tests that measure eggshell strength and these have formed the subject matter for several extensive reviews and prior art technology. The most commonly used methods to measure eggshell strength include specific gravity, shell deformation, shell thickness, shell percentage, structural properties, breaking strength, static stiffness and also a more recent method based on acoustic resonance frequency analysis for determining a non-destructive selection variable called dynamic stiffness.

In previous reports on the subject of eggshell strength it has been stated that the average egg breakage from point of lay to consumers' use was around 7%. However, despite the use of selection variables like the ones previously named, recent estimates indicate that this value has changed very little and thus, up to now, there is apparently no ideal variable for the genetic selection of laying hens for improved eggshell strength.

In EP738888 for instance a detector for determining cracks in eggshells is described. With this detector, the sound signal produced by a small ball briefly bouncing on a surface area of an egg is measured. More particularly, the curve of the sound intensity oscillating over time of the bouncing of the ball provides information about whether or not this surface area is intact. By carrying out this determination several times for the same egg, the condition of a shell of an egg, i.e. the presence or absence of cracks or ruptures in the eggshell, is mapped in an automated manner whereby a value for this condition is generated. Such a value is used as a criterion in the sorting of eggs. However, an important problem relates to the attachment of the measuring means to an egg. Such an attachment is quite difficult to manufacture. In addition, the detector disclosed in EP' 888 is not easily applied to a batch of eggs and will take a long time to process and sort the eggs.

Therefore, there is a need of a novel approach for the determination of an indicator of eggshell strength.

SUMMARY OF THE INVENTION

A need still exists for an improved method and apparatus for examining eggs.

It is an object of the present invention to provide an alternative apparatus and method for examining eggs, more specifically it is an object of the invention to provide an alternative apparatus and method for determining eggshell characteristics of eggs.

It is another object of the present invention to provide novel predictors which provide a status of an intact eggshell.

This object is met by the method and apparatus according to the independent claims of the present application. The dependent claims relate to preferred embodiments.

Advantageously, there is provided a non-destructive method for determining resistance to cracking of an intact egg, whereby said determining comprises at least one of the following steps a) and b):

a) determining a tensile stress developed in an eggshell of said intact egg, for example a tensile stress at a predetermined load;

b) determining an elasticity of said eggshell;

wherein preferably the results of step a) and/or step b) are used in evaluating said resistance to cracking.

For example, according to a further embodiment, determining a tensile stress can include calculating the tensile stress, more particularly using or based on a determined eggshell thickness and curvature of the intact egg.

In an aspect the invention provides an apparatus for non-destructively examining an egg, in particular for predicting a status of an intact eggshell, the apparatus comprising:

a detector for determining a shell thickness and/or curvature of the said eggshell and/or elasticity of said eggshell, whereby said detector provides at least an eggshell property;

a central processing unit for determining with this eggshell property a tensile stress developed in an eggshell, whereby said tensile stress is used as an predictor for a status of said eggshell.

Preferably the detector comprises a camera and/or a laser source and/or a radioactive source and/or a light source.

In an aspect the invention provides a non-destructive method for determining a tensile stress developed in an eggshell of an intact egg, whereby said tensile stress is used as a predictor for a status of said eggshell. Preferably determining a tensile stress developed in an eggshell comprises measuring a shell thickness and curvature of the said eggshell. More preferably determining a tensile stress developed in an eggshell comprises measuring elasticity of said eggshell.

In preferred embodiments elasticity of said eggshell is determined using mechanical means, for example by a mechanical detector. In alternative preferred embodiments elasticity of said eggshell is determined using optical means, for example an optical detector. Preferably, the optical means or optical detector comprises utilizing scattering and/or reflection techniques and/or computer vision and/or thermography. More preferably the optical means comprise surface Brillouin scattering or n-ray measurements or X-ray measurements.

In preferred embodiments elasticity of an eggshell is determined in a non-contact way.

The status of an eggshell preferably comprises crack presence determination and/or tensile strength and/or probability of breaking.

In preferred embodiments determining a tensile stress developed in an eggshell comprises finite element analysis comprising geometric representation and localized stress estimation. In preferred embodiments a "meta model" or a "surrogate model" is composed which preferably interpolates between simulations resulting in a prediction of all possible sorts of eggs. Preferably determining a tensile stress developed in an eggshell is performed online.

In an aspect, the present invention provides methods for sorting eggs wherein the non-destructive method for determining a tensile stress developed in an eggshell of an intact egg according to the invention is used for determining, during this sorting, the status of an eggshell of said eggs.

In an aspect, the present invention provides an apparatus for sorting eggs wherein the apparatus according to the invention is used for determining, during this sorting, the status of an eggshell of said eggs.

In an aspect, the present invention provides use of tensile stress of an eggshell of an intact egg in a non-destructive manner as a predictor for a status of said eggshell.

In an aspect, the present invention provides an apparatus for non-destructively examining an egg, in particular for predicting resistance to cracking of an intact egg, the apparatus comprising:

a detector for determining a shell thickness and/or curvature of the said eggshell and/or elasticity of said eggshell, whereby said detector provides at least an eggshell property;

a central processing unit for determining with this eggshell property a tensile stress developed in an eggshell and measuring said elasticity of said eggshell, whereby said tensile stress and elasticity are used as an predictor for a resistance to cracking of an intact egg.

For example, a said eggshell property can be indicative of or associated with the thickness of the eggshell, e.g. such that the thickness can be determined or calculated from the provided eggshell property. A said eggshell property can be indicative of or associated with the curvature of the eggshell, e.g. such that the curvature can be determined or calculated from the provided eggshell property. Also, a said eggshell property can be indicative of or associated with the elasticity of said eggshell, e.g. such that the elasticity can be determined or calculated from the provided eggshell property.

A said detector can provide said eggshell property in various ways, for example by providing a detector signal that is indicative of or contains such a property, or a detector signal that contains information concerning such property. The skilled person will appreciate that the detector and a said central processing unit can be configured to communicate with each other, using suitable communication means (e.g. a wired or wireless communication link), particularly to transmit the eggshell property (or detector signal) from the detector to the processing unit.

Preferably the apparatus is configured to determine a ratio of said tensile stress developed in an eggshell of said intact egg and said elasticity of said eggshell. Preferably the detector comprises a camera and/or light source and/or laser source and/or radioactive source.

In an aspect the present invention provides a non-destructive method for determining resistance to cracking of an intact egg, whereby said determining comprises calculating a tensile stress developed in an eggshell of said intact egg and measuring said elasticity of said eggshell.

Preferably calculating a tensile stress comprises measuring a shell thickness and curvature of the said eggshell. This can e.g. be achieved by a shell thickness detector and eggshell curvature detector, respectively. More preferably measuring said elasticity of said eggshell is performed using mechanical means. In other embodiments measuring said elasticity of said eggshell is performed using optical means. Preferably the optical means comprises utilizing scattering techniques and/or computer vision. More preferably, optical means can comprise surface Brillouin scattering, infrared imaging techniques such as e.g. thermography, more preferably active and/or passive thermography or optical coherence tomography (OCT).

Preferably thermography relates to infrared thermography (IRT) or thermal imaging or thermal video as examples of infrared imaging science. Advantageously, thermography is a non-destructive method and it is relatively fast, non-contact and provides full field information. Thermal imaging cameras detect radiation in the infrared range of the electromagnetic spectrum (roughly 9,000-14,000 nanometers or 9-14 µm) and produce images of that radiation, called thermograms. These thermograms, obtained passively or actively, are used in embodiments of the invention to provide physical parameters of an eggshell, such as e.g. elasticity and/or thickness. Preferably passive thermography is used to provide an eggshell thickness of an intact egg. Active thermography as used in embodiments of the invention provides a radiative or in other embodiments an ultrasonic source which can excite present surface cracks of an eggshell where said source is preferably pulsed infrared (IR) radiation. By applying pulsed infrared radiation the surface temperature is cyclically increased and decreased as a result of the pulsation. In addition, the absorption of IR radiation will generally decrease with increased wavelength. Most of the IR radiation is therefore reflected at the surface. As a result, when light enters a micro-crack present in an eggshell, it is reflected multiple times inside the crack and this will deposit a larger amount of energy than at a single reflection, in a similar way as in a blackbody cavity. Furthermore, according to Kirchhoff's law for a system at thermal equilibrium, the emissivity of a surface equals the absorptivity, although the wavelength of the absorbed and emitted radiation does not need to be the same. Due to these two factors, a crack in a eggshell that is illuminated by high intensity IR light will advantageously absorb and emit more energy than the surroundings and will be visible as a hot-spot if imaged by an IR camera.

Advantageously by using active thermography the size of cracks can be detected. More specifically the size of crack that can be detected depends on several factors. To be visible the crack needs to absorb enough energy in order to achieve a temperature that the IR camera can differentiate from the background. Generally the radiation from the background is uneven, because of varying emissivity, and the temperature of a crack therefore needs to be raised above this noise level. How much energy that can be absorbed depends on the width of the crack since a wider crack has a larger area where more light can enter. The width also affects what wavelengths can be absorbed in the crack, since light with a wavelength that is longer than the crack is wide will not enter the crack. Although the wavelength of the radiation will set a limit for which cracks that are detectable, it should in general be as long as possible since that will increase the contrast in absorption between a crack and the surrounding surface. A practical limit to the size of cracks that can be detected is the IR camera. The resolution of the camera together with the choice of lens will determine how small objects that can be detected. The choice of lens is a balance between resolution and field of view. Only the smallest dimension of the crack is of importance when it comes to detection; the length of the crack does not affect this methods ability to detect it.

In other preferred embodiments active thermography can also be used to measure a thickness of an eggshell, for instance one can apply a numerical inversion method and compare the results achieved. One example of such an inversion method is an iterative echo defect shape method. A second example of such an inversion method is the Levenberg-Marquardt method, which can be applied to thermographic data for non-destructive testing. Since data capturing using active thermography and the numerical inversion methods can easily be automated, the combination of these two procedures may be a promising approach providing a thickness of an eggshell.

Preferably characterizing said elasticity is determined in a non-contact way.

Preferably determining resistance to cracking of an intact egg comprises crack presence determination and/or tensile strength and/or probability of breaking.

Preferably calculating said tensile stress comprises finite element analysis comprising geometric representation and localized stress estimation. In preferred embodiments a "meta model" or a "surrogate model" is composed which preferably interpolates between simulations resulting in a prediction of all possible sorts of eggs. Preferably determining resistance to cracking of an intact egg is performed online.

In preferred embodiments a ratio of said tensile stress developed in an eggshell of said intact egg and said elasticity of said eggshell is used as a strength index to evaluate the resistance to cracking of an intact egg.

In a aspect the present invention provides a method for sorting eggs, wherein the non-destructive method for determining resistance to cracking of an intact egg according to the invention is used for determining, during this sorting, the resistance to cracking of said intact eggs.

In an aspect, the present invention provides an apparatus for sorting eggs wherein the apparatus for non-destructively examining an egg, in particular for predicting resistance to cracking of an intact egg, according to the invention is used for determining, during this sorting, the status of an eggshell of said eggs.

In an aspect, the present invention provides use of a ratio of said tensile stress developed in an eggshell of said intact egg and said elasticity of said eggshell is as a strength index to evaluate the resistance to cracking of an intact egg.

In an aspect, the present invention provides an apparatus for non-destructively and non-compactly measuring a thickness of an eggshell of an intact egg, the apparatus comprising:
  a detector for measuring a curvature of the said eggshell and/or elasticity of said eggshell and/or tensile strength developed in said eggshell, whereby said detector provides at least an eggshell property;
  a central processing unit for determining with this eggshell property, a thickness of said eggshell.

Preferably the detector comprises a camera and/or light source and/or laser source and/or radioactive source.

In an aspect, the present invention provides a method for determining a thickness of an eggshell, whereby said eggshell is an eggshell of an intact egg, whereby said thickness is determined by measuring elasticity of said eggshell or a tensile stress developed in said eggshell, whereby said determining is performed in a non-destructive and non-contact way.

Preferably elasticity of said eggshell is determined using optical means. More preferably optical means comprises utilizing scattering and/or reflection techniques and/or computer vision. In other preferred embodiments optical means comprise surface Brillouin scattering and/or β-ray measurements and/or X-ray measurements and/or thermography and/or active thermography and/or optical coherence tomography (OCT).

Determining a thickness, according to embodiments of the invention, comprises finite element analysis comprising geometric representation and localized stress estimation. Preferably said stress estimation is performed using other methods than disclosed in the embodiments of the present invention. In preferred embodiments a "meta model" or a "surrogate model" is composed which preferably interpolates between simulations resulting in a prediction of all possible sorts of eggs. Preferably determining a thickness further comprises determining a curvature of said eggshell. Preferably the curvature of said eggshell is measured in a non-contact way. In preferred embodiments, the non-contact way comprises computer vision and/or optical means.

Determining elasticity of an eggshell according to embodiments of the invention comprises determining a shell matrix modus of elasticity. Preferably said determining is performed online.

Preferably said eggshell of said eggs are brittle, for example said eggs are avian eggs. The avian egg is a biological structure of high complexity. It may contain an air chamber and a viscous liquid surrounded by two membranes and an external brittle covering which is the eggshell.

In an aspect the present invention provides a method for sorting eggs, wherein the method for determining a thickness of an eggshell according to the invention is used for determining, during this sorting, the thickness of an eggshell of said eggs.

In an aspect, the present invention provides an apparatus for sorting eggs wherein an apparatus for non-destructively and non-compactly measuring a thickness of an eggshell of an intact egg according to the invention is used for determining, during this sorting, the thickness of an eggshell of said eggs.

In an aspect, the present invention provides use of elasticity of an eggshell or tensile strength developed in an eggshell of an intact egg to measure a thickness of said eggshell in a non-destructive and non-contact way.

In an aspect, the present invention provides a computer program product for, if implemented on a control unit (e.g. a central processing unit), performing a said method according to the present invention, or a combination of these.

According to an exemplary embodiment of the present invention, there is provided a program storage device readable by machine, tangibly embodying a program of instructions executable by the machine to perform method steps for providing automatic diagnosis and decision support.

In an aspect, the present invention provides data carriers storing a said computer program product according to the present invention. The term "data carrier" is equal to the terms "carrier medium" or "computer readable medium", and refers to any medium that participates in providing instructions to a processor for execution. Such a medium may take many forms, including but not limited to, non-volatile media, volatile media, and transmission media. Non-volatile media include, for example, optical or magnetic disks, such as a storage device which is part of mass storage. Volatile media include dynamic memory such as RAM. Common forms of computer readable media include, for example, a floppy disk, a flexible disk, a hard disk, magnetic tape, or any other magnetic medium, a CD-ROM, any other optical medium, punch cards, paper tapes, any other physical medium with patterns of holes, a RAM, a PROM, an EPROM, a FLASH-EPROM, any other memory chip or cartridge, a carrier wave as described hereafter, or any other medium from which a computer can read. Various forms of computer readable media may be involved in carrying one or more sequences of one or more instructions to a processor for execution. For example, the instructions may initially be carried on a magnetic disk of a remote computer. The remote computer can load the instructions into its dynamic memory and send the instructions over a telephone line using a modem. A modem local to the computer system can receive the data on the telephone line and use an infrared transmitter to convert the data to an infrared signal. An infrared detector coupled to a bus can receive the data carried in the infra-red signal and place the data on the bus. The bus carries data to main memory, from which a processor retrieves and executes the instructions. The instructions received by main memory may optionally be stored on a storage device either before or after execution by a processor. The instructions can also be transmitted via a carrier wave in a network, such as a LAN, a WAN or the internet. Transmission media can take the form of acoustic or light waves, such as those generated during radio wave and infrared data communications. Transmission media include coaxial cables, copper wire and fiber optics, including the wires that form a bus within a computer.

In an aspect, the present invention provides in transmission of the computer program product over a network.

An object of the current invention is to propose a novel approach for the determination of a novel indicator of eggshell strength, preferably based on fundamental principles of fracture mechanics in brittle materials. More specifically the analysis of a concentrated force on a spherical shell. Transferring the analysis and behavior of brittle materials such as metals to eggs, is not straightforward for a person skilled in the art because such a person would not search in a remote field as brittle metal analysis for a solution to analyze the breaking behavior of an egg and more specifically use the physical properties of an eggshell to provide novel indicators of eggshell strength.

Moreover, using a tensile strength in an eggshell and/or elasticity of an eggshell as an indicator or predictor of eggshell strength have not been disclosed in any prior art documents known to the applicant. In addition, the ratio of these indicators, providing yet another novel indicator of eggshell strength, has not been disclosed in any prior art documents known to the applicant. Furthermore, these theorems and material analysis tools, have been known since 1959 and earlier, however since then the urgent need of providing an approved eggshell strength indicator has not been fulfilled by any prior art documents.

BRIEF DESCRIPTION OF THE DRAWINGS

Further features of the present invention will become apparent from the examples and figures, wherein.

DEFINITIONS

In this application the term "intact egg" can be defined as an undamaged or unfractured egg in its whole, thus an egg in one piece whereas the eggshell itself can be damaged, for instance comprising micro and/or macro-cracks.

In this application, the term "eggshell" can be defined as brittle eggshells, whereby said brittle eggshells when subjected to stress, preferably break without significant deformation (strain). Brittle materials preferably absorb relatively little energy prior to fracture, even those of high strength. Brittle materials include most ceramics and glasses, which preferably do not deform plastically such as for instance sea-urchin eggs which deform plastically when external forces are applied.

In this application, particularly, a "tensile stress" can be defined as a tensile stress under a predetermined load, e.g. a certain external force (N) (see FIGS. 1, 2) that is exercised onto the egg. The tensile stress in particular can lead to an internal expansion of the material.

In this application, the term "eggshell strength" may relate to a parameter describing how well the egg can withstand external loads. The term can be expressed for eggs as deformation for a given load, or the breaking strength. Also, the probability of breaking of an egg under practical circumstances can be taken as a (practical) way of describing eggshell strength, as will be clear to the skilled person.

The "breaking strength" can be defined as the amount of external load the egg can withstand before it fails (i.e. breaks, ruptures).

"Stiffness" can be defined as the force required to deform the egg with one deformation unit. "Static stiffness" can be defined as said force under (quasi-) constant loading conditions. "Dynamic stiffness" can be defined as said force under changing loading conditions, such as an impact.

"A breakage" can be defined as a macroscopic failure of the shell of the egg. "A crack" can be defined as a micro/macroscopic failure of the shell of the egg.

"Elasticity" can be defined as a measure for the stiffness of an elastic material, defined as ratio between the stress and strain, as is commonly known to the skilled person.

Figure 1:
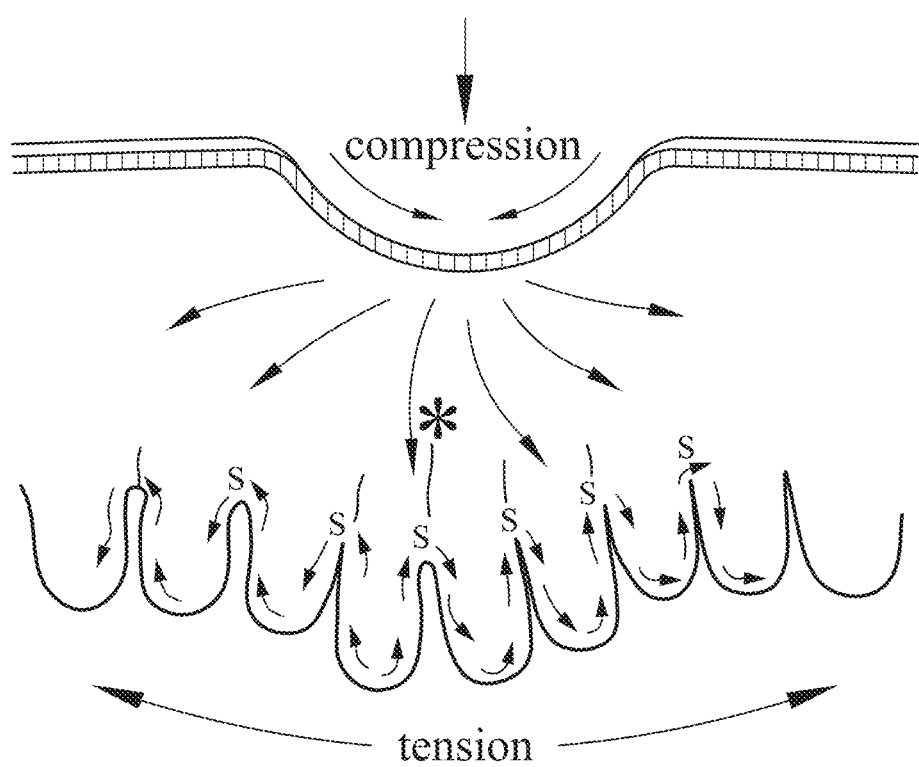
FIG. 1 schematically illustrates the failure mechanism in eggshells, whereby failure begins with the accumulation of tensional stress (s) where adjacent calcite columns fuse. A crack then quickly propagates through the shell wall towards the outer surface (*).
Figure 2:
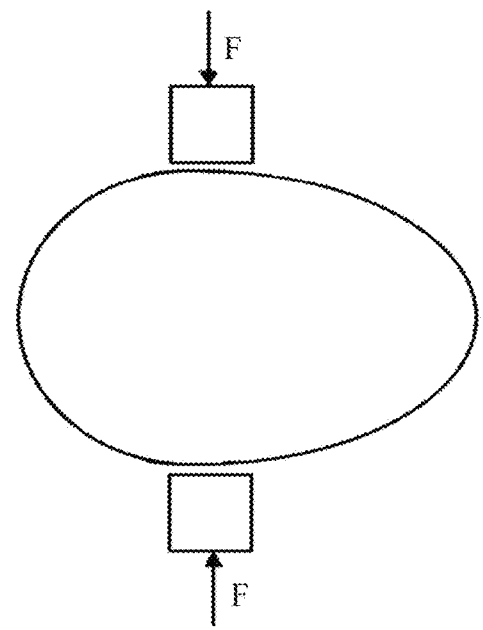
FIG. 2 schematically illustrates the base model according to embodiments of the invention.
Figure 3:
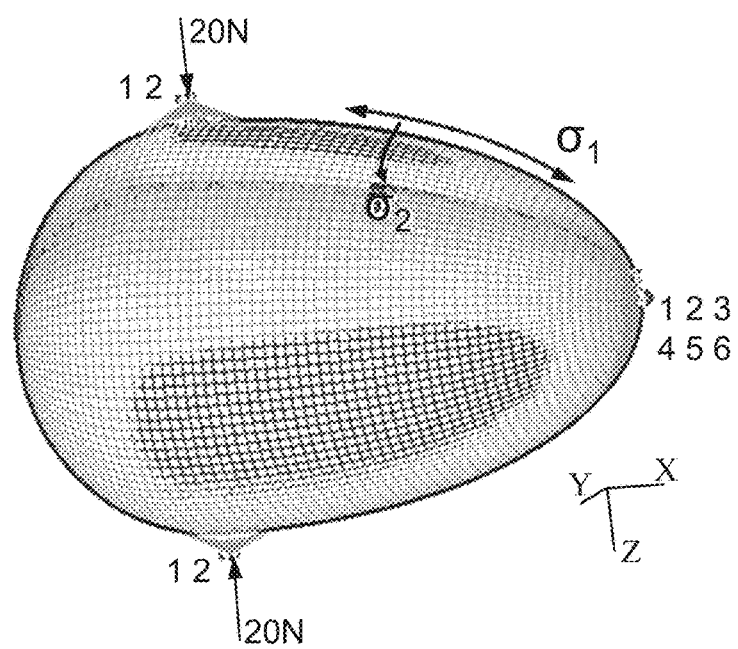
FIG. 3 illustrates a finite element mesh model of an eggshell according to embodiments of the invention.

"Tensile stress" can be defined as stress leading to an internal expansion of the material, e.g. due to external loading (see e.g. FIGS. 1-3). "Strain" can mean: deformation relative to the initial size. "Shear stress" can be: stress causing an object to skew.

"A probability of breaking" can be defined as the proportion of eggs that will fail under a predefined external load.

"Damping ratio" can mean: a measure for the (loading) energy absorption capability of the egg.

DETAILED DESCRIPTION OF PREFERRED EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

The term "comprising", used in the claims, should not be interpreted as being restricted to the means listed thereafter; it does not exclude other elements or steps. Thus, the scope of the expression "an apparatus comprising means A and B" should not be limited to an apparatus consisting only of components A and B. It means that with respect to the present invention, relevant components of the apparatus are A and B.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

In the drawings, like reference numerals indicate like features; and, a reference numeral appearing in more than one figure refers to the same element. The drawings and the following detailed descriptions show specific embodiments of the apparatus and methods for examining eggs.

In order to understand the fracture behaviour of the eggshell material, embodiments of the invention are based on the mechanisms of fracture of materials that are entirely brittle, more specifically based on the mechanisms of fracture of metals, which are known to be brittle.

A brittle material, such as an eggshell, when it is subjected to stress, breaks without significant deformation (strain). Brittle materials absorb relatively little energy prior to fracture, even those of high strength. Thus, a ductile metal rod subjected to axial tension undergoes plastic deformation and becomes progressively thinner in the middle until the concentration of tensile stresses makes it fracture. On the other hand, a rod of brittle material when subjected to similar tensile stress would fracture instantly without undergoing plastic deformation. Because shear stresses cause deformation in plastic material prior to fracture, the maximum tensile stresses are critical for causing fracture of brittle material such as an egg.

Brittle materials in general are stronger under compressive forces than under tensile ones, as the molecules are pressed closely during compression. Furthermore, the most important failure criteria in modern engineering are those which take account of a materials resistance to crack growth since it is now generally accepted that most structures contain cracks or flaws, introduced during manufacture or initiated early in their life. A complete understanding of the reaction of the eggshell to external forces requires knowledge of the stress distribution and the effect of this on naturally formed flaws in the ultrastructure. Classical engineering theories indicate that failure occurs when the maximum principal stress in any structure attains a critical level.

Using this approach, it has been concluded that the tensile stresses are at a maximum at the inner surface of the eggshell directly beneath the loading point (FIG. 1), and predicted that failure initiated at this site when the tensile stress, $\sigma_r$, reached the theoretical cohesive strength, $\sigma_{th}$. Consequently, the derived eggshell failure criterion can be written in the form:

$$\sigma_r \geq \sigma_{th}. \tag{1}$$

Embodiments of the present invention provide adapting the analysis of a concentrated force on a flat plate for the case of a spherical shell by Timoshenko and Woinoswley-Krieger of 1959 on an egg and whereas the spherical shell represent the egg geometry, this result in an expression of the tensile stress on the inner shell surface beneath the force as:

$$\sigma_t = \frac{F}{t^2}\left[0.559(1+v)\log_{10}\frac{R}{t} + 0.3 + 0.59v\right], \quad (2)$$

Where F (in Newton) is the force applied to the spherical shell, t (in m) is the shell thickness, v is the Poisson ratio of the shell material and R (in m) the curvature radius of the shell.

The tensile stress, $\sigma_t$, is the maximum stress caused by the applied force and the eggshell will fracture when this stress reaches the theoretical strength, $\sigma_{th}$, of the shell material. Commonly, initial failure in the shell occurs under conditions of tensile stress and is located at the inner surface of the shell under the loading point.

As described in the Griffith's theory of brittle fracture (1921), the fracture strength of a brittle material is a function of the cohesive forces that hold the atoms together. Thus, the right term of the eggshell failure criterion, the theoretical cohesive strength, $\sigma_{th}$, of a brittle elastic solid like the eggshell in this context, is theoretically estimated as E/10, where E is the modulus of elasticity or the Young modulus of the shell material. However, according to practical observations, the fracture strengths of real materials are much lower, normally 10 to as much as 1000 times below their theoretical values as a consequence of the internal flaws, introduced during manufacture or initiated early in their life. These internal defects lower the fracture strength of the material because they amplify the stress at the crack tip.

Embodiments of the present invention provide that when evaluating the strength of an eggshell two common properties are preferably used to define its ability to withstand forces or deformations: the tensile stress developed in the eggshell and/or the Young/elastic modulus of the shell material.

Using Tensile Stress Developed in an Eggshell as a Predictor for Evaluating the Strength of an Eggshell according to Embodiments of the Invention Until now, eggshell tensile stress has been evaluated in many studies by using other analytical and experimental techniques known for eggs and eggshells. According to reported results the tensile stress at failure ranged from 15 to 35 MPa. Moreover, by means of combined analytical and experimental approaches, it was found that the stress developed at each point in a shell exposed to some environmental insult is strongly related to the thickness and curvatures of the shell. More recently, some complex studies investigating the stress distribution in eggshells by means of finite elements confirmed the experimental findings previously mentioned.

Advantageously embodiments of the invention provide an automatic measurement system of a tensile stress in an egg which can be deduced from Equation 2, that requires the Poisson ratio, the shell thickness and the curvature of the shell to be quantified. As the Poisson ratio is commonly considered to be a constant with a value of 0.307 only two other egg parameters are needed to enable a measure of a tensile stress in an egg, namely the shell thickness and the curvature of the shell. Advantageously these two remaining parameters can be measured in a non-destructive way, resulting in a novel way to measure tensile stress in a non-destructive way.

Until now methods used in the prior art to obtain the tensile stress in an egg are based on methods which are destructive and which induce damage to the eggshell while trying to measure the needed parameters. For instance the method disclosed by Macleod et al in Int. Journal of Fract. Vol. 142 p. 29-41 (2006) to measure a tensile strength and internal pressure. The method by Macleod et al comprises using a hypodermic syringe filled with water which is used to internally pressurize an egg which is sealed with a polyurethane varnish. This method introduces damage to the eggshell and does not enable a predictor to evaluate the strength of an eggshell. In addition the method provided by Macleod et al is not easily and rapidly applied for a batch of eggs to be tested and/or sorted.

In addition, the remaining parameters can be measured in a non-destructive way and preferably in a non-contact way, by for instance measuring or deducing a shell thickness and/or the curvature of the shell based on optical measurement means, for instance utilizing scattering and/or reflection techniques and/or computer vision and/or thermography (or thermographic printing) and/or active thermography and/or a β-ray back-scattering device and/or OCT based techniques. Whereby a different source can be used to detect a physical property of the egg, like e.g. a light source, an ultrasound source and/or a thermal source and/or a radioactive source. A combination of these techniques advantageously can render the shell thickness and/or the curvature of the shell in a non-destructive and non-contact way.

In alternative embodiments the thickness can be also be measured with a calliper or by using Hertz theory as disclosed in WO/2012/060704. It is known to a skilled person that a variation in eggshell thickness will result in a variation of vibration frequencies, e.g. generally a thicker eggshell results in higher frequencies of vibration. This is because an increase in eggshell thickness strengthens the shell stiffness and this increases the natural frequency. Similarly, a reduction in size of an egg can reduce its mass and, consequently, the resultant resonant frequency can increase. Preferably, eggshell thickness and resonant frequency are almost linearly related, whilst mass and resonant frequency can show a more pronounced nonlinear relation.

Since the specific gravity of an intact egg is closely correlated with shell thickness, specific gravity measurements can be used to determine a thickness and thus the shell strength, this is a non-destructive way to measure a thickness of an eggshell however using specific gravity of an intact egg as a method to determine a thickness of an eggshell is very time consuming. In addition when using specific gravity as a method to determine a thickness of an intact eggshell, the age of the egg can introduce difficulties when interpreting the measurement results. For instance a not-freshly laid egg can comprise an enlarged air cell which complicates the distinguishing features between the properties of the egg, namely the enlarged air cell and the thickness of the egg.

Of course contact means to measure the two remaining parameters can also be applied according to alternative embodiments of the present invention. The curvature of the shell can be measured with e.g. a tripod and related trigonometry. Or using computer vision or thermography. What concerns the shell thickness, it can be assessed using for instance a digital micrometer after opening of the shell with high precision. In addition ultrasound based techniques can be used, which are a viable technique for monitoring eggshell thickness. Moreover, ultrasonic instruments like the Egg Shell Thickness Gauge (www.eggtester.com) are nowadays available on the market and such a tool can measure thickness at various points on the shell without resorting to the traditional time-consuming method of breaking the egg and measuring individual segments. Thickness can be measured over a range of 0.15 mm to 25 mm with a sensitivity of 0.001 mm. Several authors also mention a moderate but significant correlation between shell thickness and static stiffness (correlation ~0.8) measured during quasi static compression between two parallel plates using a universal testing machine. However, such static stiffness measurement system is time consuming and is not suitable for online purposes. For instance WO/2012/060704 describes an online measurement system that aims at determining the static stiffness and shell thickness in an online way. In WO'704 good correlations could obtained with reference values.

In other preferred embodiments the evaluation of tensile stresses developed in the eggshell at certain load values is provided, to enable the latter a high accuracy modeling approach is presented. More preferably an online estimation of tensile stresses are presented.

Finite element analysis according to embodiments of the invention is used which combines highly accurate geometric representation and localized stress estimation and is therefore the most suitable option for such application. The current model simulates how two parallel circular plates apply a distributed constant force on both sides of the eggshell as illustrated in FIG. 2. Consequently, the loading deforms the eggshell which generates a complex stress path within the eggshell. The purpose of the analysis is to estimate the tensile stresses on the inside as well as on the outside of the shell for egg models of different dimensions loaded with a force of an assumed constant value of 20 N as illustrated in FIG. 3. The eggshell thickness is assumed to be uniform over the shell surface, e.g. a default value can be applied (for example 0.38 mm). The material parameters of an eggshell used in this embodiment are as follows: Young's modulus $E=3*1010$ N m$^{-2}$, Poisson's ratio $v=0.307$ and the mass density $\rho=2400$ kg m$^{-3}$. The finite element meshes as illustrated in FIG. 3 are preferably generated using MSC. Patran (MSC Software, Santa Ana, Calif., USA). In preferred embodiments, finite element analysis is performed which is a linear static analysis where the relationship between the forces [F] and the displacements [X] is described by a stiffness matrix [K] as expressed in Eq. 3:

$$[F]=[K]\cdot[X] \quad (3)$$

This matrix equation is preferably solved using the Newmark solver incorporated in MSC. Nastran (MSC Software, Santa Ana, Calif., USA) as described in detail by Geradin and Cardona (2001). Finally, using the simulation output, a multiple linear regression model is preferably set-up. The covariates are the two radii of curvature of the egg (i.e. the major radius of curvature and the minor radius of curvature) and the eggshell thickness. The tensile stress serves as an output variable. Thus, the derived model according to preferred embodiments of the invention for the prediction of the tensile stress is given by $$\sigma_1 = -4.486392 + 1.58625666 \cdot r_1 + 1740.138 \cdot \frac{1}{t} - 0.839939 \cdot r_2 \quad (4)a$$

where $\sigma_1$ is the predicted tensile stress response; $r_1$ is the major curvature radius and $r_2$ is the minor curvature radius. With this relation, it is possible to estimate an alternative indicator of eggshell strength, the tensile stress, using classical geometrical measurements of curvature and thickness. The above formula for the tensile stress is based on the measurement of the egg curvatures (both long as short axis), complemented by knowledge about the shell thickness. As indicated before the shell thickness can be estimated or measured by various techniques, such as ultrasound measurements and vibration analysis of the egg. Evidently, classical computer vision techniques or thermography or light scattering techniques can be used in order to determine radii of curvature with high precision The skilled person will appreciate that formula 4(a) for the predicted tensile stress response can be generalized as follows:

$$\sigma_1 = K_1 + K_2 \cdot r_1 + K_3 \cdot t^{-1} + K_4 \cdot r_2 \quad (4b)$$

wherein $K_1$, $K_2$, $K_3$, $K_4$ are constants that can be derived from the above-mentioned equations as has been explained above.

Using the Young/Elastic Modulus of the Shell Material as a Predictor for Evaluating the Strength of an Eggshell according to Embodiments of the Invention As indicated above two eggshell properties are preferably used to define the ability of an egg to withstand forces or deformations, the tensile stress developed in the eggshell as illustrated in Eq. 2 and/or the Young/elastic modulus of the shell material.

Determination of a Young modulus according to embodiments of the invention can involve the use of an extensometer mounted on a standard specimen of defined shape and size. The next step can consist in loading the specimen by stretching, compressing or twisting under specified conditions and the force-deformation couples recorded during the test provide a direct measure of the elastic constants and failure stresses. Unfortunately, such a test cannot be applied to measure the eggshells' elastic modulus due to its brittle nature, its curvature and also the important variation in eggshell thickness. However, several studies have attempted to determine the Young modulus of the eggshell by various indirect means and in most cases this has involved the adaptation of existing engineering theories in which the modulus can be obtained from an analysis of the stresses and strains induced under some form of loading. As reported in their studies the Young modulus of the shell material ranged from 15 to 55 GPa. These studies can be found in the following two references: Rehkugler, G. E. (1963). Modulus of elasticity and ultimate strength of the hen's egg shell. Journal of Agricultural Engineering Research, 8, 352e354; and: Kemps, B., De Ketelaere, B., Bamelis, F. R., Govaerts, T., Mertens, K., Tona, K., Decuypere, E., & De Baerdemaeker, J. (2004). Development of a methodology for calculation of Young's modulus of eggshell using vibration measurements. Biosystems Engineering, 89, 215e221.

Specialized set-ups to measure the Young modulus of eggshells have been extensively described in the prior art, although the direct measures have a destructive nature and are hence not applicable to online quality control of eggs. For instance by using finite element analysis to analyze the stresses and strains in models of the eggshell under quasi-static compressive loads and developed formulae to calculate the elastic modulus of the eggshell. These formulae use the data derived from quasi-static compression tests and allow direct comparisons to be made, since differences in shape, curvature and thickness (structural properties) are taken into account in the calculation. Also performing dynamic measurements in order to determine the elastic modulus of a shell segment can be used. A technique which was developed and preferably can be used to determine the elasticity of an eggshell, according to embodiments of the invention, comprises exciting a shell segment and measure its resonant frequency. This resonant frequency together with the dimensions of the shell segment form the base for the calculation of the dynamic elastic modulus. A formula for the elastic modulus can be derived, according to embodiments of the invention, using modal analysis of a shell segment.

In alternative embodiments as indicated compression can be applied to obtain E-modulus values for an eggshell or by using $k_{stat}$. In other embodiments this can also be accomplished by applying Hertz theory as described in WO/2012/060704.

Embodiments of the present invention also provide using surface Brillouin scattering (or stimulated Brillouin scattering), where you stimulate surface acoustics waves, to obtain properties of the egg shell, more specifically to obtain the elastic properties of an eggshell. Surface Brillouin Scattering (SBS) is a non-contact measurement technique that exploits light scattering to probe the properties of surface acoustic waves (SAWs), either at the surface of homogeneous solids or in thin supported layers. The near-surface elastic properties of solids often differ markedly from those of the underlying bulk material. They are a sensitive indicator of residual stress, annealing and other near-surface physical conditions. SBS is widely used in the characterization of thin (sub-micron) supported layers, whose elastic properties can differ from those of the corresponding bulk material. It can alternatively be exploited to measure other properties, like the layer thicknesses or mass density, or the presence of interfacial layers. The systems that have been studied to date are many and diverse, and include inorganic materials like silicon and silicides, a variety of carbonaceous materials like diamond, CVD diamond and diamond-like films, various types of hard coatings like carbides and nitrides, Langmuir-Blodgett films, and various types of multilayers. SBS can probe acoustic waves of frequencies up to 100 GHz and characterize films of thickness as thin as a few tens of nanometers.

The present invention provides embodiments whereby a numerical model is used to determine the Young modulus, whereby said number model represents a simplified replica of a chicken egg, a fluid filled shell, yielding a coupled structural-acoustic problem. Here, the eggshell is modeled as a single layer shell structure of uniform thickness. The acoustic content includes the air chamber and water, the major component of albumen (~90%) and yolk (~50%). The shell membranes are not incorporated in the model. The numerical approach, according to embodiments of the invention, used for the representation of the coupling effects between fluid and structure is based on a Finite Element (FE) representation of the structure as well as the interior fluids. The main advantage of such a method is that is easily possible to represent in one model cavities with different types of fluid, e.g. water and air.

Figure 4:
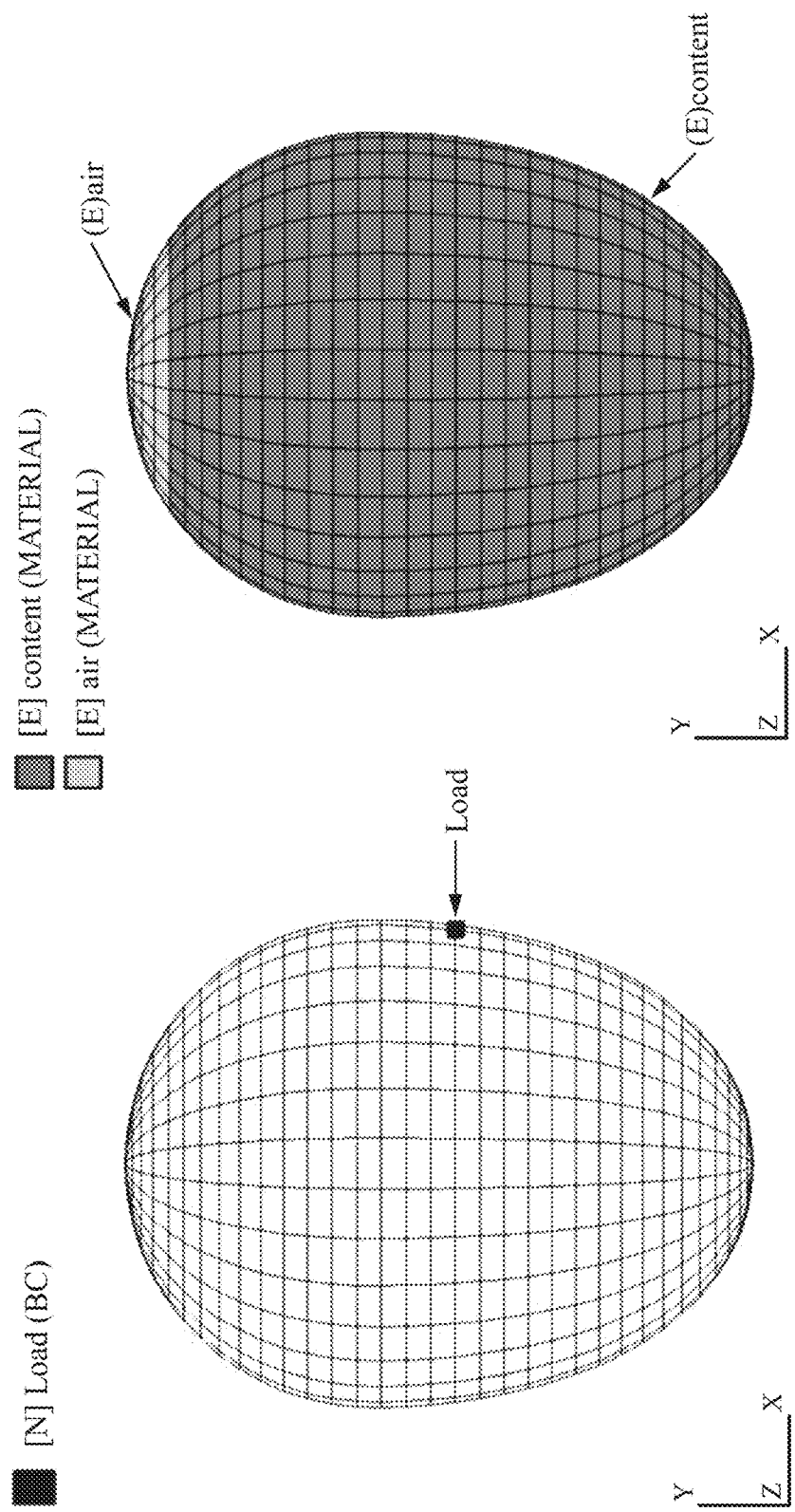
FIG. 4 illustrates a finite element mesh of the eggshell (left) and of its acoustic content (right) according to embodiments of the invention.

The base model preferably represents a simplified replica of a chicken egg. The egg-shaped geometry is preferably approximated by a half-ellipsoid fused to a half-sphere. The overall dimensions of the egg model can be 4.6, 5.8 and 4.6 cm, respectively in X (longitudinal), Y (vertical) and Z (lateral) direction. Preferably eggshell thickness is assumed to be uniform over the shell surface. A default value of 0.38 mm was applied. The material parameters of the eggshell are as follows: Young's modulus E=3*1010 N m$^{-2}$, Poisson's ratio ν=0.307 and the mass density ρ=2400 kg m$^{-3}$. The egg content was represented by an air chamber and a water domain. The height of the air chamber for the default configuration is preferably 4 mm. The acoustic parameters of the air are preferably: speed of sound 343 m s$^{-1}$ and the mass density 1.25 kg m$^{-3}$. The default values for the acoustic parameters of water are: speed of sound 1500 m s$^{-1}$ and the mass density 997 kg m$^{-3}$. The finite element meshes, as illustrated in FIG. 4, for both structural and acoustic domain were preferably generated using MSC. Patran (MSC Software, Santa Ana, Calif., USA).

All uncoupled structural results are preferably obtained with the MSC. Nastran software, while the acoustic and coupled vibro-acoustic results are obtained with the LMS. Sysnoise software (LMS International, Leuven Belgium). The structural-acoustic model involved in the simulations was a free boundary condition model excited by a unit normal point force exerted at the egg equator as illustrated in FIG. 4.

For the fluid filled egg, the obtained resonant frequencies of the coupled modes were close to the experimental results. Moreover, the mode shapes and the sequence of appearance of the calculated modes were very similar to the experimentally observed modes. Based on the simulation output, a multiple linear regression model is provided set-up according to embodiments of the invention. The covariates preferably are the resonant frequency of the egg, the eggshell thickness and the two radii of curvature of the egg. The Young modulus serves as an output variable. Finally, the prediction formula for the Young modulus of the eggshell is given by $$E=-9.285398+1.4190459 \cdot r_1+1.7592802 \cdot r_2-0.007557 \cdot t+0.0014944 \cdot RF \quad (5)$$

where E is the predicted Young modulus; $r_1$ is the major curvature radius, $r_2$ is the minor curvature radius, t is the shell thickness and RF is the resonant frequency.

In other embodiments of the invention, the above described formula (Eq. 5) for the Young modulus can be based on the measurement of the egg curvatures (both long as short axis), complemented by knowledge about the shell thickness and resonant frequency of the egg.

The skilled person will appreciate that formula (5) for the predicted Young modulus can be generalized as follows:

$$E=K_5+K_6 \cdot r_1+K_7 \cdot r_2+K_8 \cdot t+K_9 \cdot RF \quad (5)'$$

wherein $K_5$, $K_6$, $K_7$, $K_8$ are constants that can be derived from the above-mentioned equations as has been explained above.

Using the Ratio of the Tensile Stress and Young/Elastic Modulus of the Shell Material as a Predictor for Evaluating the Strength of an Eggshell according to Embodiments of the Invention Since the Young modulus of the eggshell is three orders of magnitude (GPa) greater than its tensile fracture strength (MPa), the right term of the eggshell failure criterion (equation 1), the theoretical cohesive strength, $\sigma_{th}$, should be equal to E/1000. Such lower value for the fracture strength of the eggshell represents a direct consequence of the flaws present in the eggshell (e.g. pores, microcracks). The resulting eggshell failure criterion can now be written as:

$$\sigma_t \geq E/1000 \quad (6)$$

Thus from the failure criterion we can conclude that $\sigma_t$ depends on the curvature and thickness of an eggshell whereas $\sigma_{th}$ depends on the material characteristics of the eggshell of an egg.

Eq. 6 can then be redistributed in the following form:

$$E/(1000\sigma_t) \leq 1, \quad (7)$$

According to preferred embodiments of the invention, the ratio of the two novel predictors, $(E/1000\sigma_t)=k_{new}$, provides yet another novel eggshell strength index. Or taking into account Equation 1 this can also be written as $k_{new}=\sigma_{th}/\sigma_t$.

In further advantageous embodiments of the present invention, one can adapt Griffiths equation, which describes the relationship between applied nominal stress and crack length at fracture, i.e. when it becomes energetically favorable for a crack to grow, to enable estimation of the properties of such a crack, like for instance crack length. As Griffith provides a measure for the energetics of fracture, and considered the energy changes associated with incremental crack extension, these properties can be integrated in a later phase. For instance for a loaded brittle body undergoing incremental crack extension, the only contributors to energy changes are the energy of the new fracture surfaces (two surfaces per crack tip) and the change in potential energy in the body. The surface energy term (S) represents energy absorbed in crack growth, while the some stored strain energy (U) is released as the crack extends (due to unloading of regions adjacent to the new fracture surfaces). Surface energy has a constant value per unit area (or unit length for a unit thickness of body) and is therefore a linear function of (crack length), while the stored strain energy released in crack growth is a function of (crack length)$^2$, and is hence parabolic. These changes can be quantified using the theorems provided above in a next step.

In addition, as the next step in the development of Griffith's argument was consideration of the rates of energy change with crack extension, because the critical condition corresponds to the maximum point in the total energy curve, i.e. dW/da=0, where a=a*, for crack lengths greater than this value (under a given applied stress), the body is going to a lower energy state, which is favorable, and hence fast fracture occurs, thus providing a measure of crack resistance. dW/da=0 occurs when dS/da=dU/da and R is the resistance to crack growth (=dS/da) and G is the strain energy release rate (=dU/da). When fracture occurs, R=G and we can define a novel predictor according to embodiments of the invention, namely $G_{crit}$ as the critical value of strain energy release, and equate this to R. Hence $G_{crit}$ advantageously represents the fracture toughness of an eggshell.

Use of Novel Predictors according to Embodiments of the Invention as a Means to Measure a Thickness of an Eggshell in a Non-Destructive and preferably Non-Contact Way As indicated above Equations 4 and 5, 5' are both dependent on the thickness of an eggshell. If one would re-write the equations in order to obtain the thickness of an eggshell, the dependency of the eggshell thickness in function of the tensile strength and elasticity of the eggshell become apparent. A thickness of an eggshell, whereby said eggshell is an eggshell of an intact egg, can be determined by measuring elasticity of said eggshell or a tensile stress developed in said eggshell, whereby said determining is can performed in a non-destructive and preferably non-contact way.

Preferably elasticity of an eggshell is determined using optical means, which enable determination in a non-contact way. For example optical means can be used based on scattering and/or reflection techniques and/or computer vision and/or thermography or thermographic printing. Preferably elasticity of an eggshell is determined using SBS.

Advantageously, embodiments of the present invention, provide three novel predictors to evaluate the strength of an eggshell, namely tensile strength of an eggshell, elasticity of an eggshell and a ratio of the tensile strength and elasticity of an eggshell. In addition, embodiments of the invention provide novel ways to determine a thickness of an intact egg, in a non-destructive way and preferably in a non-contact way.

Figure 14:
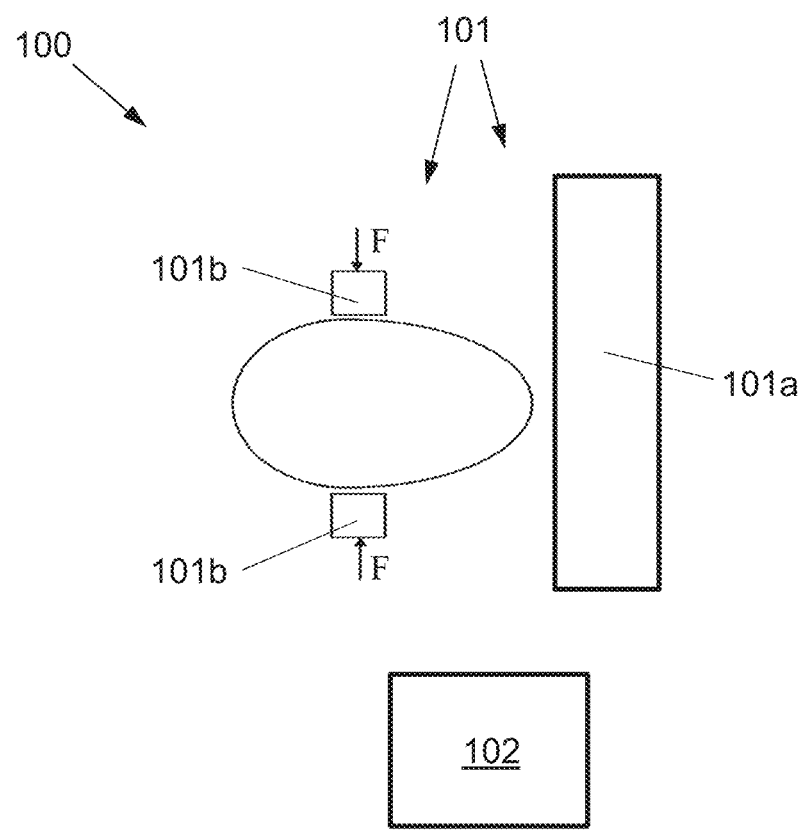
FIG. 14 schematically illustrates an embodiment of an apparatus.

FIG. 14 schematically illustrates a non-limiting embodiment of an apparatus 100, that includes one or more above-mentioned detector(s) 101, and a central processing unit 102, the apparatus being configured for carrying out a method according to the invention. According to an embodiment, the apparatus 100 can be an apparatus for non-destructively examining an egg, in particular for predicting a status of an intact eggshell. In an embodiment, the apparatus 100 can be an apparatus for non-destructively examining an egg, in particular for predicting resistance to cracking of an intact egg. In addition or alternatively, the apparatus 100 can be an apparatus for non-destructively and non-contactly measuring a thickness of an eggshell of an intact egg The (at least one) detector 101 may be configured for determining a shell thickness and/or curvature of the said eggshell and/or elasticity of said eggshell, whereby said detector provides at least an eggshell property. Examples of such detectors 101 are described above. The detector may e.g. include one or more non-contact detector units 101a (e.g. optical detector means), and/or e.g. one or more contact detector units 101b (e.g. mechanical means, mass detector, load applicator, test bench).

Also, the (at least one) detector 101 may be configured for measuring a curvature of the said eggshell and/or elasticity of said eggshell and/or tensile strength developed in said eggshell, whereby said detector provides at least an eggshell property.

In an embodiment, the central processing unit 102 can be configured for determining with this eggshell property a tensile stress developed in an eggshell and determining said elasticity of said eggshell, whereby at least one of said tensile stress and elasticity, preferably both, are used as an predictor for a resistance to cracking of an intact egg.

In an embodiment, the central processing unit 102 can be configured to determine with said eggshell property a tensile stress developed in an eggshell, whereby said tensile stress is used as an predictor for a status of said eggshell.

In addition or alternatively, the central processing unit 102 can be configured to determine with this eggshell property, a thickness of said eggshell.

The central processing unit 102 can be implemented in various ways, for example in hardware and/or software, as well be cleat to the skilled person.

As is mentioned before, a detector 101 and central processing unit 102 can be configured to communicate with each other, using suitable communication means (e.g. one or more wired and/or wireless communication links), particularly to transmit the eggshell property (or detector signal) from the detector 101 to the processing unit 102.

Experimental Results

This section below describes the results of a series of experimental tests designed to provide that the three strength indices used as predictors according to preferred embodiments of the invention are better eggshell strength estimator than classical measures know in the art like e.g. egg weight, shell thickness, shape index, static or dynamic stiffness.

By way of illustration, embodiments of the present invention not being limited thereto, an example of a validation of a method and system according to embodiments of the present invention is described and experimental results are discussed below.

Chicken eggs from a commercial flock were collected the day of lay from hens that were around 55 weeks old. The eggs were inspected on the Acoustic Egg Tester and only eggs that were clean (no visible faecal, egg content or other dirt on the shell) and intact (no hairline cracks, cracks or pinholes) were used in the study. Finally, 200 eggs covering all sizes (M, L and XL) were selected and stored under ambient conditions (20-25° C.) for one day before use Throughout the experiment, several methods are used for the assessment of the physical and mechanical eggshell properties. The mass (m) of the eggs was measured with an electronic weighing balance with an accuracy of 0.1 g. Eggshell thickness (t) was measured as the average thickness of three equidistant points on the equator of each egg using a micrometer gauge with spherical tips. The resolution of this equipment was 1 μm. Length and width were measured with a sliding digital caliper (precision 0.01 mm), and the shape index (SI) was calculated as the ratio between length and width in all the eggs.

Figure 5:
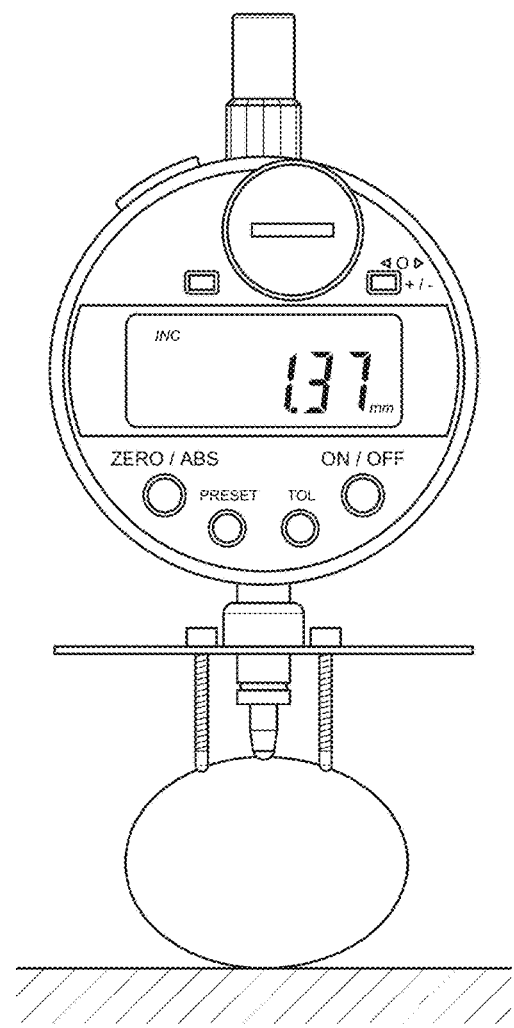
FIG. 5 illustrates a radius of curvature meter using a Mitutoyo® height meter.

The two radii of curvature of the egg ($r_1$ and $r_2$) were measured locally at the egg equator by a radius of curvature meter as illustrated in FIG. 5.

To find the static stiffness of the eggshell, the eggs were compressed on a universal test-bench (UTS Testsysteme GmbH, Germany) until a maximal load of 10 N. The measurement remains non-destructive since the average compression force value needed for egg breakage is around 35 N. Eggs were placed horizontally between two flat parallel steel plates and compressed at a speed of 10 mm/min. The resolution of the force sensor was 0.001 N. Force [N] and displacement [mm] were recorded throughout the test and used to calculate the static stiffness ($k_{stat}$). The slope of the force-displacement curve provides a measure of the eggshell static stiffness.

Figure 6:
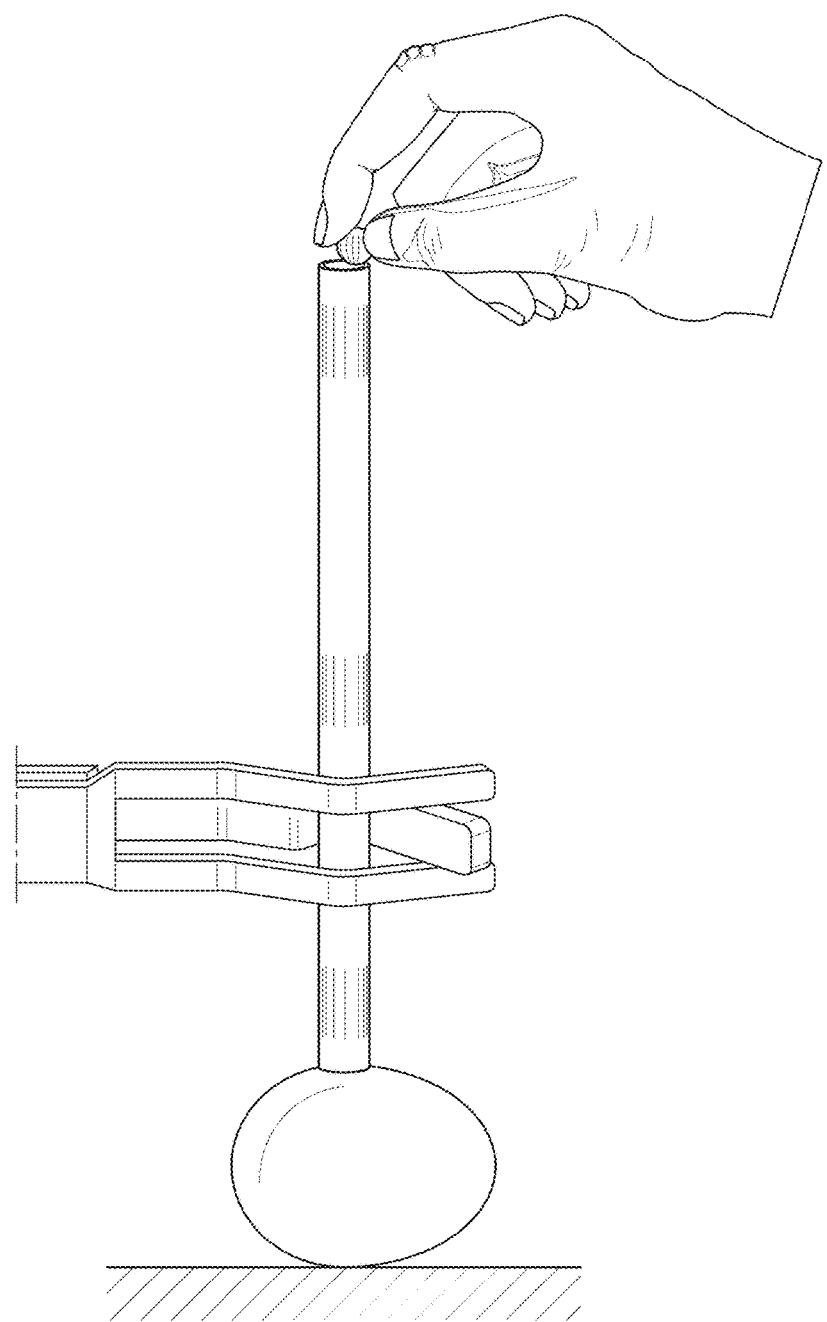
FIG. 6 illustrates the falling ball experimental set-up.

The measurement of the dynamic stiffness ($k_{dyn}$) is done with the Acoustic Egg Tester (AET). Modeling the egg as a mass-spring system, the dynamic stiffness is given as:

$$k_{dyn} = cte. \times m \times RF^2, \qquad (8)$$

with m the mass of the egg in kg, cte. a constant (set to 1) and RF the first resonant frequency of the vibration in Hz. Moreover, this technique measures the damping ratio of the egg (δ) and can also be used to detect cracks in the eggshell. Finally, tensile stress, Young modulus and eggshell strength index of the eggshell were determined by inserting the measured values of the two radii of curvature, thickness and resonant frequency in the prediction formula presented in the previous sections. On the other hand, to be able to find the most significant parameters for eggshell strength, cracks were created in an artificial way by using a falling ball technique as illustrated in FIG. 6. As can be seen from FIG. 6, a metal ball with a mass of 3 grams is dropped vertically through a tube with a length of 18 cm onto the eggshell surface, and it falls under the influence of gravity. The use of such guiding tube helps to maintain a constant falling height for all measurements, independent of the size of the egg.

Results were statistically evaluated using Microsoft Office Excel 2007 and Matlab R2009b. The statistical study consisted in applying an One-Way Univariate ANOVA test (Analysis Of Variance) to make the actual comparison between individual parameters based on the corresponding P-values. A significance level of 5% was imposed in the model. The p-value is the probability of obtaining a test statistic at least as extreme as the one that was actually observed, assuming that the null hypothesis is true. One often "rejects the null hypothesis" when the P-value is less than the significance level α, which is often 0.05 or 0.01. When the null hypothesis is rejected, the result is said to be statistically significant.

The percentage of cracked eggs obtained after the falling ball test was around 40%. As mentioned earlier, the results were statistically processed using Matlab and visualized as box-plots. Firstly, a model was built to investigate the difference in shape index between intact and cracked eggs.

Figure 7:
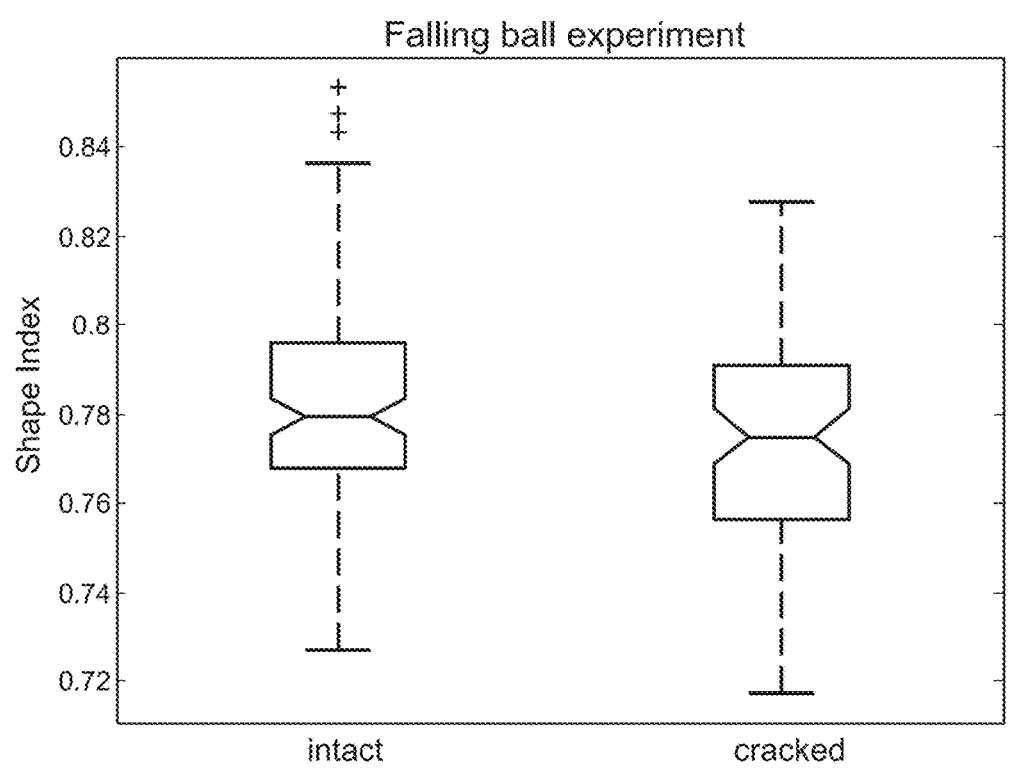
FIG. 7 illustrates the significance of shape index as an eggshell strength estimator rendering a P-value of 0.006.

A significance level of 5% was used in the model, meaning that if the calculated P-value is lower than 0.05 the difference between shape index of intact eggs and shape index of cracked eggs is significant. As shown in FIG. 7 the shape index of intact eggs was significantly higher than the one of cracked eggs. The obtained P-value of 0.006 indicates a significant difference between the shape index for intact and cracked eggs. Moreover, as it can be derived from the boxplot, intact shells are rounder than cracked shells. This trend is physically correct since the stress induced in the eggshell by the impact force is better distributed and therefore better supported by a rounder shell structure.

Figure 8:
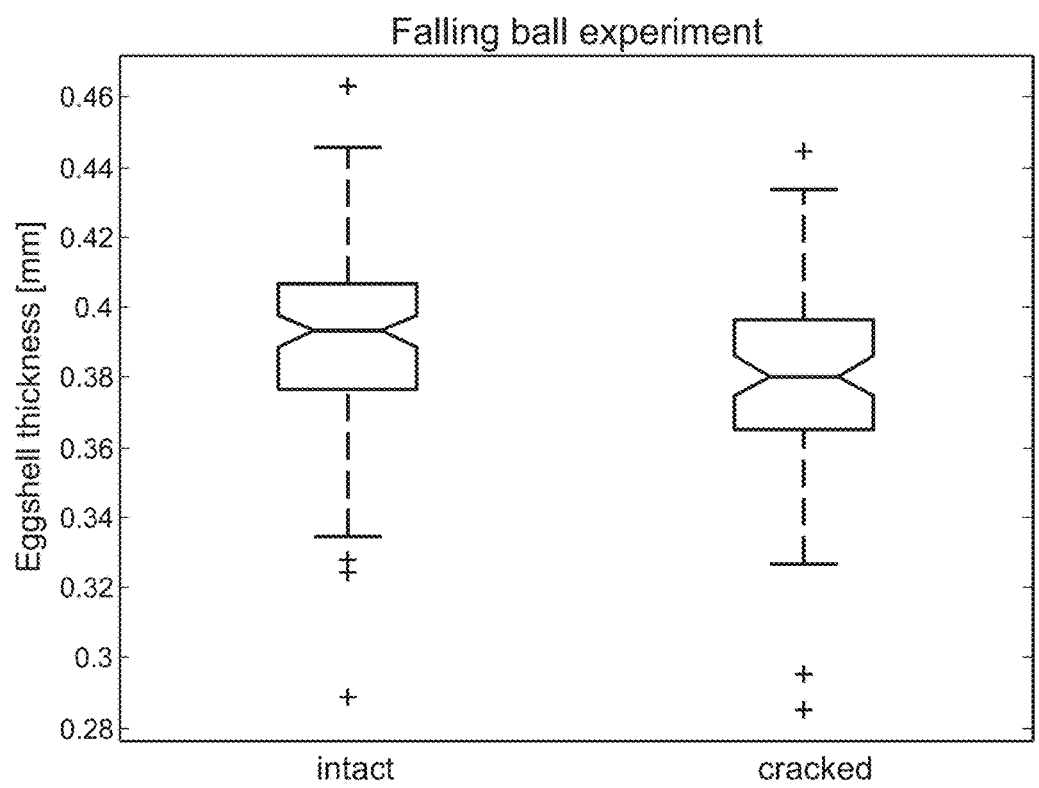
FIG. 8 illustrates the significance of eggshell thickness as an eggshell strength estimator rendering a P-value of 0.004.

FIG. 8 shows the box-plot of the eggshell thickness. Analyses revealed that the eggshell thickness of intact eggs was significantly higher than the one of cracked eggs. From FIG. 8 it can be concluded that cracked eggshells are thinner than intact shells. This was also expected, considering that thicker shells resist better than thinner shells to various loading cases.

Figure 9:
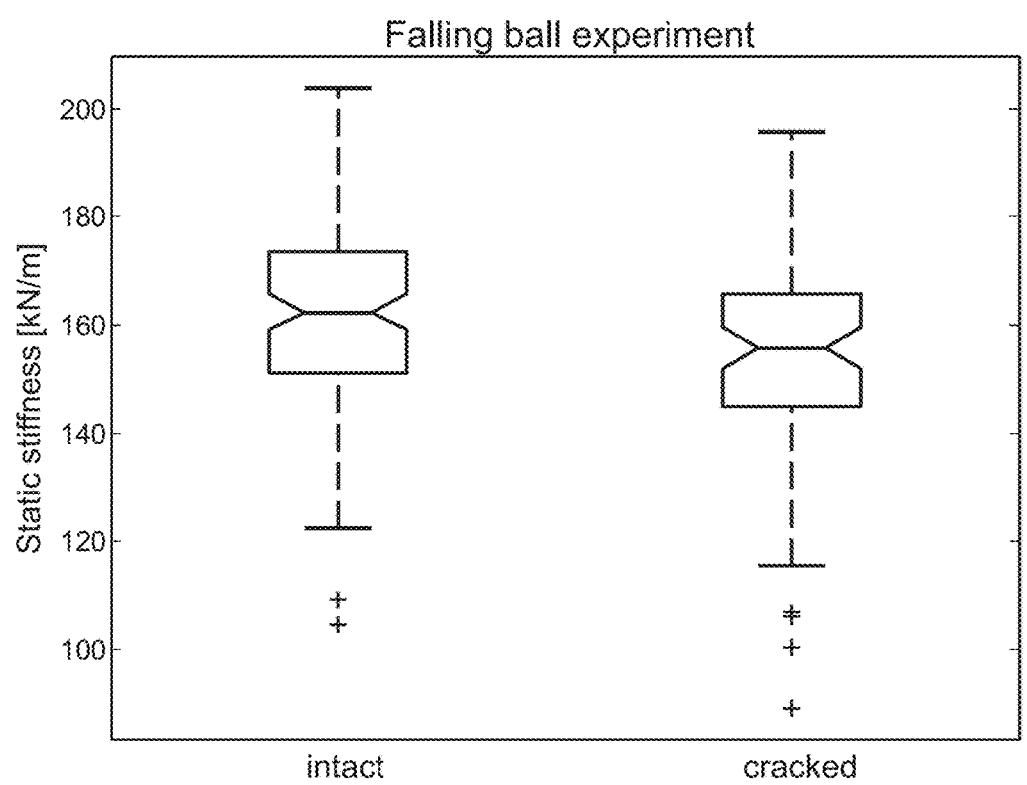
FIG. 9 illustrates the significance of static stiffness ($k_{stat}$) as an eggshell strength estimator rendering a P-value of 0.004.
Figure 10:
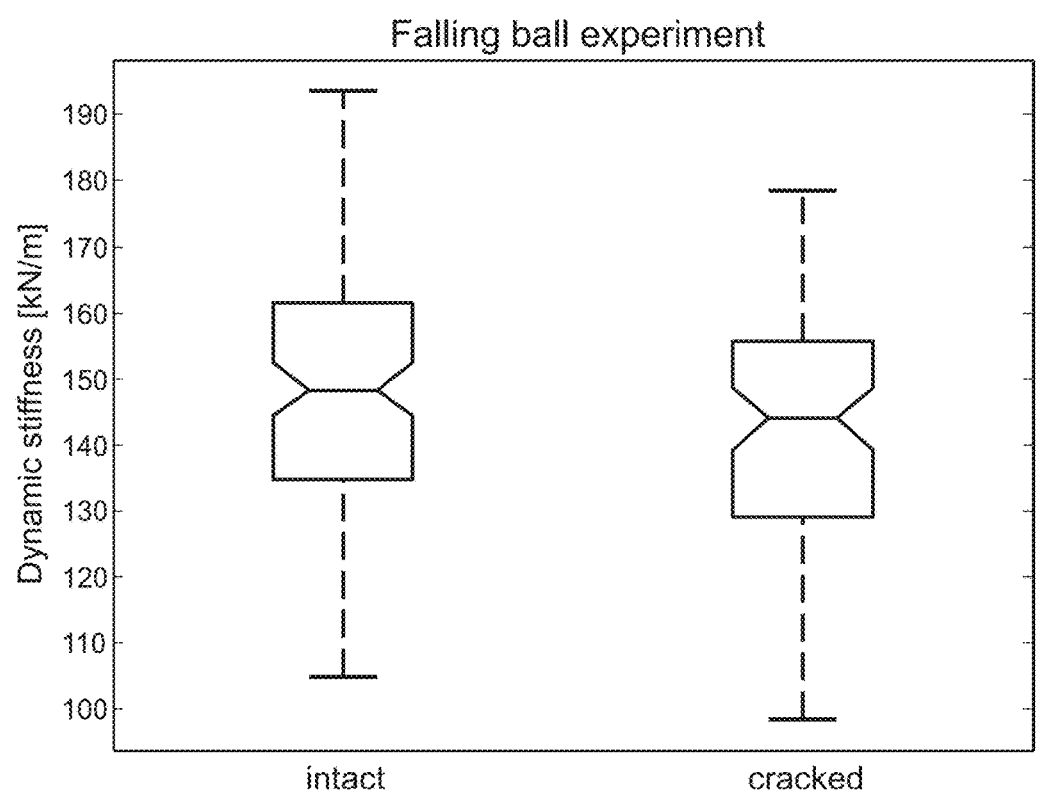
FIG. 10 illustrates the significance of dynamic stiffness ($k_{dyn}$) as an eggshell strength estimator rendering a P-value of 0.06.

FIG. 9 and FIG. 10 illustrate the box-plots of respectively static and dynamic stiffness. The resultant P-value for static stiffness (P=0.004) demonstrates that static stiffness of the eggshell is a highly significant parameter for eggshell strength. On the other hand, despite its P-value (0.06) slightly superior to the significance level, dynamic stiffness remains one of the important indicators of eggshell strength. However, such weak significance can be explained by the fact that dynamic stiffness is directly related to resonant frequency and this parameter was clearly non-significant (P=0.4) in this experiment. Commonly, the resonant frequencies of materials actually reflect on the strength and distance between atoms in the material and thus, the non-significance level of resonant frequency in this experiment can be justified by the fact that although the eggs used in this experiment answered very well to the geometrical variation demand, those eggs were unfortunately coming from a single flock which represented in fact a limiting factor in material variation.

Figure 11:
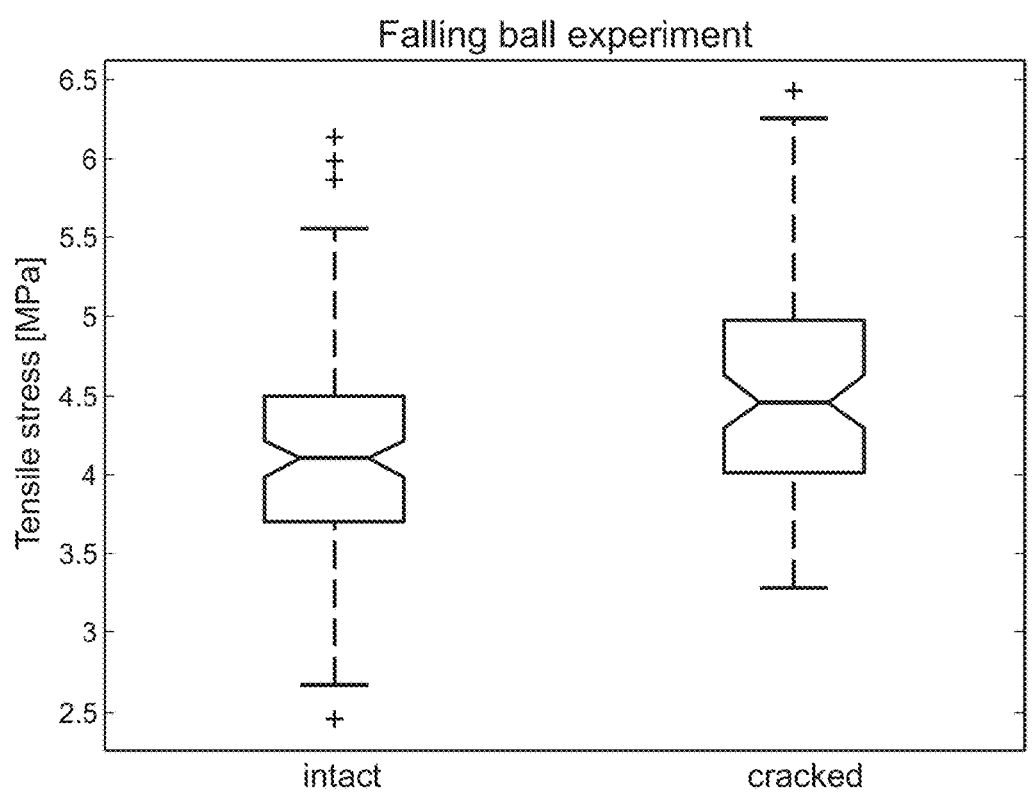
FIG. 11 illustrates the significance of tensile stress as an eggshell strength estimator, according to embodiments of the invention, rendering a P-value of 0.00007.

In FIG. 11 the box-plot visualization of the differences in tensile stress between intact and cracked eggs are illustrated. The P-value of 0.00007 indicates that this new strength indicator according to embodiments of the invention, the tensile stress, is a significant parameter in dynamic breakage of eggs by the falling ball technique, much more significant (2 orders of magnitude of difference in P-value) than the previously mentioned classical strength indicators. As presented in FIG. 11, cracked eggs had higher stress values when compared to intact eggs. A totally logical trend since higher stress values represent increased chances in reaching the failure stress levels. As expected, combining curvature and thickness of the eggshell in one parameter, the tensile stress, offers a more complete picture in terms of eggshell strength.

Figure 12:
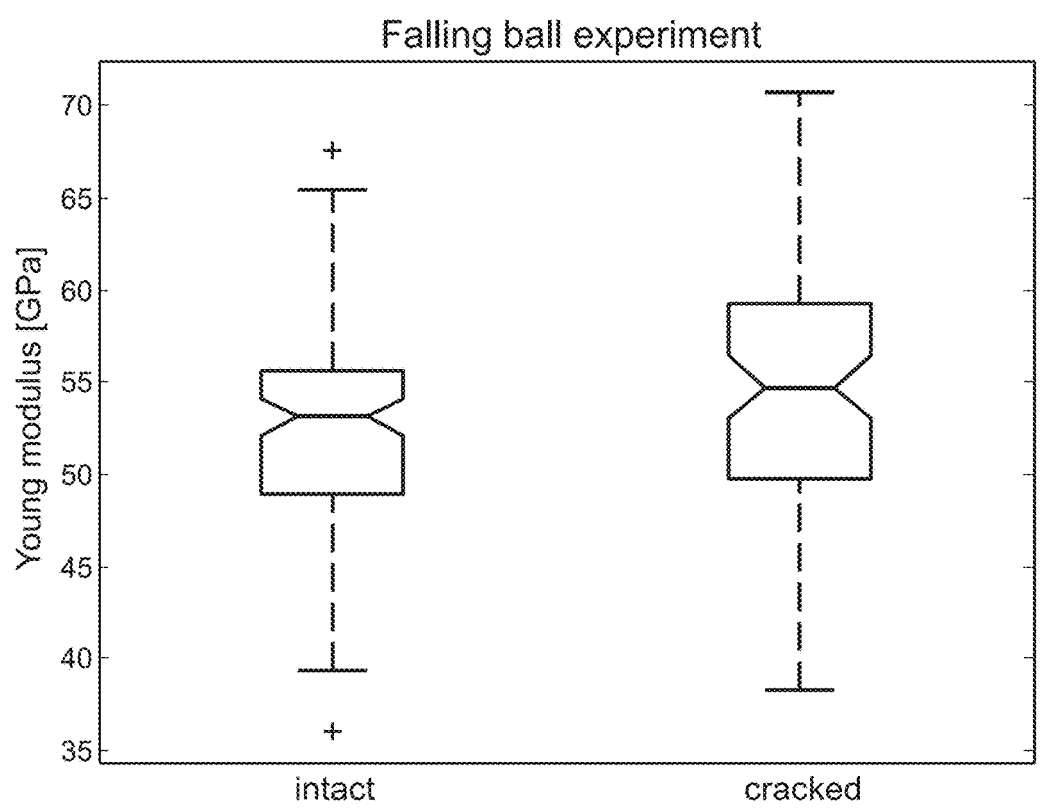
FIG. 12 illustrates the significance of Young modulus/elasticity of an eggshell as an eggshell strength estimator, according to embodiments of the invention, rendering a P-value of 0.05.

In addition, FIG. 12 shows the variation in Young modulus, as a new strength indicator, between intact and cracked shells. With a P-value of exactly 0.05, the Young modulus can be considered as a significant parameter for eggshell strength with the mention that this clearly represents a weak significance factor. Additionally, it should also be stressed that the expected trend was to have lower Young modulus values for the cracked eggs while the obtained results showed an opposite evolution. Since the prediction formula of Young modulus combines geometrical and material parameters (e.g. curvature radii, thickness and resonant frequency), the results can be explained the same way as the ones for dynamic stiffness. Consequently, a new experiment with good material variation of the measured eggs (eggs coming from different flocks) should improve both significance and evolution of Young modulus.

Figure 13:
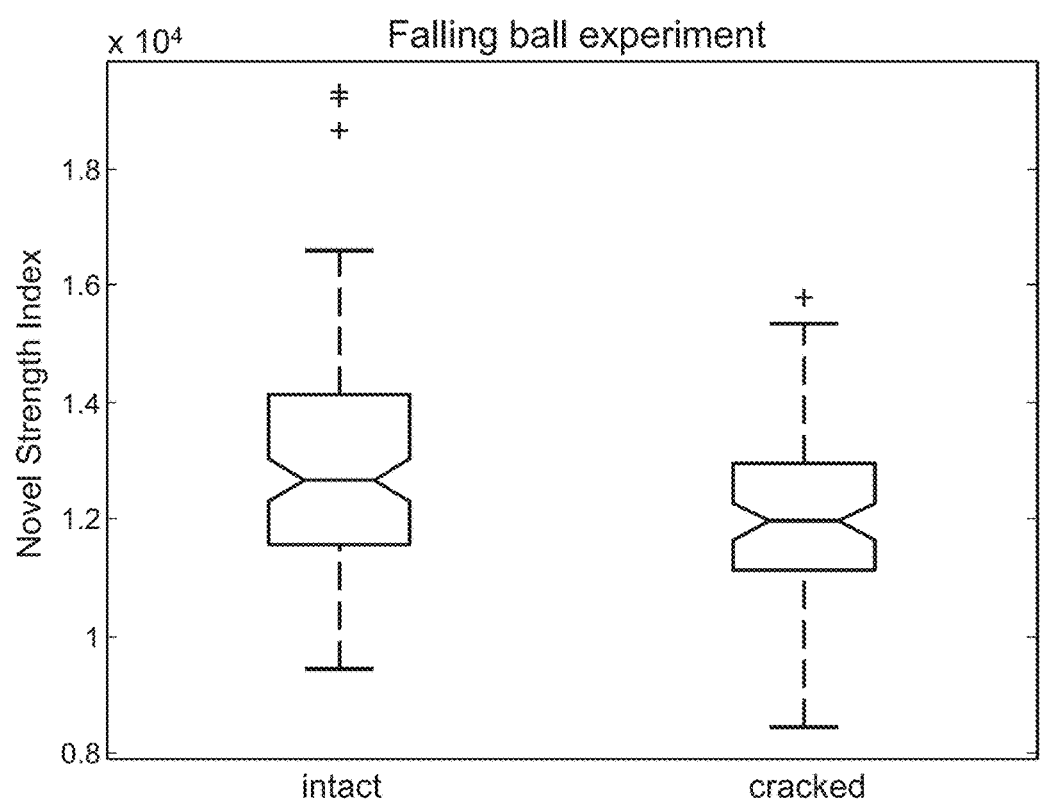
FIG. 13 illustrates the significance of $k_{new}$ as an eggshell strength estimator, according to embodiments of the invention, rendering a P-value of 0.0009.

Finally, a model was built to investigate the difference in $k_{new}$, which is dependent on the ratio of the tensile strength and the elasticity of an eggshell according to embodiments of the invention, between intact and cracked eggs. As shown in FIG. 13 the $k_{new}$ of intact eggs was significantly higher than the one of cracked eggs. The obtained P-value of 0.0009 indicates a significant difference between the shape index for intact and cracked eggs. Together with the tensile stress, $k_{new}$ offers a better measure of eggshell strength compared to classically used indicators like mass of the egg, eggshell thickness, static or dynamic stiffness. Moreover, the significance power of $k_{new}$ will normally be improved by just considering the adjustments proposed in the previous paragraph.

The present experimental work clearly demonstrates the capacity of the tensile strength, elasticity/young modulus and $k_{new}$, defined as the ratio between Young modulus and tensile stress, to better estimate the strength of the eggshell.

According to the observations of the present study, a new experiment should be designed by increasing the number of eggs and trying to have both geometrical variation (uniform distribution of eggs of different sizes) and material variation (eggs coming from several flocks) in order to validate and even improve the current findings. Further investigations can also be carried out to determine whether or not the $k_{new}$ is a better eggshell strength estimator than classical measures like specific gravity, shell deformation, shell thickness, shell percentage, breaking strength, static or dynamic stiffness and if, by incorporating the $k_{new}$ measurement into genetic selection programmes, eggshell quality will improve and the number of eggs downgraded due to cracked and damaged shells will be reduced.

It is to be understood that this invention is not limited to the particular features of the means and/or the process steps of the methods described as such means and methods may vary. It is also to be understood that the terminology used herein is for purposes of describing particular embodiments only, and is not intended to be limiting. It must be noted that, as used in the specification and the appended claims, the singular forms "a" "an" and "the" include singular and/or plural referents unless the context clearly dictates otherwise. It is also to be understood that plural forms include singular and/or plural referents unless the context clearly dictates otherwise. It is moreover to be understood that, in case parameter ranges are given which are delimited by numeric values, the ranges are deemed to include these limitation values.

For example, one or more detectors can be implemented for determining a shell thickness and/or curvature of the said eggshell and/or elasticity of said eggshell.

The invention claimed is:

1. A non-destructive method for determining resistance to cracking of an intact egg, the method comprising:
   providing the intact egg;
   determining, via a curvature meter, a curvature of an eggshell of said intact egg;
   determining, via a central processing unit, a shell thickness said eggshell of said intact egg;
   determining, via a central processing unit, a tensile stress developed in an eggshell of said intact egg at a predetermined load;
   determining, via a central processing unit, an elasticity of said eggshell;
   determining, via a central processing unit, a resistance to cracking parameter based on a ratio R of said tensile stress developed in said eggshell of said intact egg and said elasticity of said eggshell; and
   sorting a plurality of intact eggs based in the resistance to cracking parameter.

2. The method according to claim 1, wherein determining said elasticity of said eggshell is performed using mechanical means.

3. The method according to claim 1, wherein determining said elasticity of said eggshell is performed using optical means.

4. The method according to claim 3, wherein using optical means comprises at least one of utilizing scattering techniques and computer vision.

5. The method according to claim 3, wherein using optical means comprise surface Brillouin scattering.

6. The method according to claim 3, wherein characterizing said elasticity is determined in a non-contact way.

7. The method according to claim 1, wherein calculating said tensile stress comprises measuring a shell thickness and curvature of the said eggshell.

8. The method according to claim 1, wherein determining resistance to cracking of said intact egg comprises at least one of crack presence determination, tensile strength, and probability of breaking.

9. The method according to claim 1, wherein calculating of said tensile stress comprises finite element analysis comprising geometric representation and localized stress estimation.

10. The method according to claim 1, wherein the ratio R of said tensile stress developed in an eggshell of said intact egg and said elasticity of said eggshell is used as a strength index to evaluate the resistance to cracking of an intact egg.

11. The method according to claim 1, further comprising determining a status of said eggshell using said tensile stress.

12. The method according to claim 11, wherein determining said tensile stress comprises measuring a shell thickness and curvature of the said eggshell.

13. The method according to claim 11, wherein determining said tensile stress comprises measuring elasticity of said eggshell.

14. The method according to claim 13, wherein characterizing said elasticity is determined in a non-contact way.

15. The method according to claim 13, wherein said elasticity of said eggshell is determined using mechanical means.

16. The method according to claim 13, wherein said elasticity of said eggshell is determined using optical means.

17. The method according to claim 16, wherein using optical means comprises utilizing at least one of scattering techniques, reflection techniques, computer vision, and thermography.

18. The method according to claim 16, wherein said optical means comprise surface Brillouin scattering, β-ray measurements, or X-ray measurements.

19. The method according to claim 11, wherein said status of said eggshell comprises crack presence determination, tensile strength, and probability of breaking.

20. The method according to claim 11, wherein determining said tensile stress comprises finite element analysis comprising geometric representation and localized stress estimation.

21. An apparatus for non-destructively predicting resistance to cracking of an intact egg, the apparatus comprising:
    a detector configured to determine a shell thickness and curvature of an eggshell for each of said plurality of intact eggs and an elasticity of said eggshell for each of said plurality of intact eggs, whereby said detector is configured to provide at least an eggshell property and to transmit the eggshell property; and a central processing unit that is configured to receive the eggshell property from the detector, wherein the central processing unit is configured to:
determine a tensile stress developed in said eggshell for each of said plurality of intact eggs using the eggshell property for each of said plurality of intact eggs,
determine said elasticity of said eggshell for each of said plurality of intact eggs,
determine a resistance to cracking parameter to facilitate sorting said plurality of intact eggs, the resistance to cracking parameter determined based on a ratio R of said tensile stress developed in said eggshell for each of said plurality of intact eggs and said elasticity of said eggshell for each of said plurality of intact eggs.

22. The apparatus according to claim 21, whereby said detector comprises at least one of a camera, light source, laser source, and radioactive source.

23. The apparatus according to claim 21 wherein the central processing unit is further operative for determining a status of an eggshell of said eggs during a sorting process.

24. The apparatus according to claim 21, wherein the central processing unit is further operative for predicting a status of said intact eggshell.

25. The apparatus according to claim 24, whereby said detector comprises at least one of a camera, a laser source, a radioactive source, light source.

26. A method for determining a thickness of an eggshell of an intact egg, comprising: measuring an elasticity of said eggshell or a tensile stress developed in said eggshell in a non-destructive and non-contact way,
wherein said elasticity of said eggshell is determined using optical means, and
wherein said optical means comprise at least one of surface Brillouin scattering, β-ray measurements, and X-ray measurements.

27. The method according to claim 26, wherein determining said thickness comprises finite element analysis comprising geometric representation and localized stress estimation.

28. The method according to claim 26, further comprising determining a curvature of said eggshell.

29. The method according to claim 28, wherein said curvature of said eggshell is measured in a non-contact way.

30. The method according to claim 29, wherein said non-contact way comprises at least one of computer vision and optical means.

31. The method according to claim 26, wherein determining said elasticity of an eggshell comprises determining a shell matrix modus of elasticity.

32. A method for sorting a plurality of intact eggs, wherein the sorting is based on a sorting parameter, the method comprising:
providing the plurality of intact eggs;
determining a tensile stress developed in an eggshell of each of said plurality of intact eggs at a predetermined load;
determining an elasticity of said eggshell of each of said plurality of intact eggs using surface Brillouin scattering, β-ray measurements, or X-ray measurements; and
determining said sorting parameter, said sorting parameter being a ratio R for each of said plurality of intact eggs, the ratio R based on said tensile stress developed in said eggshell and said elasticity of said eggshell of each of said plurality intact egg,
sorting said plurality of intact eggs base on said sorting parameter.

33. A non-destructive method for determining resistance to cracking of an intact egg, the method comprising:
determining a tensile stress developed in an eggshell of said intact egg at a predetermined load;
determining an elasticity of said eggshell;
determining, online via a central processing unit, a resistance to cracking parameter based on a ratio R of said tensile stress developed in said eggshell of said intact egg and said elasticity of said eggshell; and
sorting a plurality of intact eggs based on the resistance determined online to cracking parameter.

34. The method according to claim 33, further comprising determining, via a curvature meter, the curvature of an eggshell of said intact egg.

35. The method according to claim 33, further comprising determining the shell thickness of said eggshell of said intact egg.

36. An apparatus for sorting a plurality of intact eggs, the apparatus comprising:
a detector configured to determine a shell thickness and curvature of said eggshell and elasticity of said eggshell, whereby said detector is configured to provide at least an at least one eggshell property of an intact eggshell and transmit the at least one eggshell property; and
a central processing unit configured to receive the at least one eggshell property from the detector, the central processing unit further configured to:
determine a tensile stress developed in said eggshell for each of said plurality of intact eggs using the at least one eggshell property for each of said plurality of intact eggs,
determine said elasticity of said eggshell for each of said plurality of intact eggs,
determine a resistance to cracking based on a ratio R of said tensile stress developed in said eggshell for each of said plurality of intact eggs of said intact egg and said elasticity of said eggshell for each of said plurality of intact eggs, and wherein said ratio R is used as a predictor for a resistance to cracking of an intact egg, and
sort said plurality of intact eggs based on said resistance to cracking for each of said plurality of eggs.

* * * * *